United States Patent
Katoh et al.

(10) Patent No.: US 11,250,297 B2
(45) Date of Patent: Feb. 15, 2022

(54) TRAINING APPARATUS, TRAINING METHOD, AND NON-TRANSITORY COMPUTER-READABLE RECORDING MEDIUM

(71) Applicant: FUJITSU LIMITED, Kawasaki (JP)

(72) Inventors: Takashi Katoh, Kawasaki (JP); Kazuki Iwamoto, Osaka (JP); Kento Uemura, Kawasaki (JP); Suguru Yasutomi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 86 days.

(21) Appl. No.: 16/774,100

(22) Filed: Jan. 28, 2020

(65) Prior Publication Data

US 2020/0242412 A1 Jul. 30, 2020

(30) Foreign Application Priority Data

Jan. 30, 2019 (JP) .............................. JP2019-014035

(51) Int. Cl.
| | | |
|---|---|---|
| *G06K 9/62* | (2006.01) | |
| *G16H 30/40* | (2018.01) | |
| *G06N 20/00* | (2019.01) | |
| *G06T 7/00* | (2017.01) | |

(52) U.S. Cl.
CPC ............ *G06K 9/6262* (2013.01); *G06N 20/00* (2019.01); *G06T 7/0012* (2013.01); *G16H 30/40* (2018.01); *G06T 2207/20081* (2013.01); *G06T 2207/20084* (2013.01); *G06T 2207/30096* (2013.01)

(58) Field of Classification Search
CPC .. G06K 9/6256; G06K 9/6271; G06K 9/6262; G06K 2209/05; G06K 9/6257; G06K 9/6259; G06K 9/6267; G06K 9/6234; G06K 9/00288; G06K 9/00624; G06K 9/3208; G06K 9/4628; G06K 9/6269; G06K 9/627; G06K 2209/01; G06K 9/00268
USPC ....................................................... 382/128
See application file for complete search history.

(56) References Cited

U.S. PATENT DOCUMENTS

2019/0198156 A1* 6/2019 Madani ................ G06N 3/0472

OTHER PUBLICATIONS

Thomas Schlegl et al., "Unsupervised Anomaly Detection with Generative Adversarial Networks to Guide Marker Discovery", Proceedings of IPMI, Mar. 17, 2017 [12 pages].
Mohammad Sabokrou et al., "Adversarially Learned One-Class Classifier for Novelty Detection", Proceedings of IEEE Conference on Computer Vision and Pattern Recognition, May 24, 2018 [10 pages].
EESR—The Extended European Search Report for European Patent Application No. 20152622.5 dated Jul. 1, 2020.

(Continued)

*Primary Examiner* — Ajibola A Akinyemi
(74) *Attorney, Agent, or Firm* — Fujitsu Patent Center

(57) ABSTRACT

An anomaly detection apparatus performs training for the generator and the discriminator such that the generator maximizes a discrimination error of the discriminator and the discriminator minimizes the discrimination error The anomaly detection apparatus stores, while the training is being performed, a state of the generator that is half-trained and satisfies a pre-set condition, and retrains the discriminator by using an image generated by the half-trained generator that has the stored state.

4 Claims, 17 Drawing Sheets

(56) References Cited

OTHER PUBLICATIONS

Antonia Creswell, et al., "Generative Adversarial Networks: An Overview", arXiv.org, Cornell University Library, Oct. 19, 2017, XP080829988.
Yaxing Wang, et al., "Transferring GANs: Generating Images from Limited Data", International Conference on Financial Cryptography and Data Security; [Lecture Notes in Computer Science; Lect.Notes Computer], Springer, Oct. 6, 2018, pp. 220-236, XP047488191.

\* cited by examiner

TRAINING APPARATUS, TRAINING METHOD, AND NON-TRANSITORY COMPUTER-READABLE RECORDING MEDIUM

CROSS-REFERENCE TO RELATED APPLICATION

This application is based upon and claims the benefit of priority of the prior Japanese Patent Application No. 2019-014035, filed on Jan. 30, 2019, the entire contents of which are incorporated herein by reference.

FIELD

The embodiments discussed herein are related to a training apparatus, a training method, and a training program.

BACKGROUND

In recent years, in the field of medical image analysis or the like, an anomaly, such as a lesion, is detected using image data. In particular, in the field of medicine or the like, it is often difficult to obtain image data of anomalous states for use for training data; therefore, there is a demand for machine training using only image data of normal states and there is also a demand for an increase in a detection speed in order to handle large amounts of precise and large-scale data.

In the circumstances as described above, as an anomaly detection method using machine training, generative adversarial networks (GANs) for estimating a distribution of normal data and detecting data deviating from the distribution as anomalous data have been known. FIG. 17 is a diagram for explaining a GAN. As illustrated in FIG. 17, the GAN is a training model that includes a generator and a discriminator and that is for unsupervised training in which a network for training the generator and a network for training the discriminator are trained simultaneously.

In the GAN, the generator is trained to generate fake data that is similar to real data from input data, such as noise, and the discriminator is trained to discriminate whether the data generated by the generator is real data or fake data. As anomaly detection using the GAN, a method of determining whether a trained generator has a capability to generate a given sample and regarding generated data as anomalous data if the trained generator does not have the capability, and a method of regarding data that is determined as fake data by the trained discriminator as anomalous data are used.

Non Patent Document 1: Schlegl, Thomas, et al. "Unsupervised anomaly detection with generative adversarial networks to guide marker discovery.", International Conference on Information Processing in Medical Imaging. Springer, Cham, 2017.

Non Patent Document 2: M. Sabokrou, et al. "Adversarially Learned One-Class Classifier for Novelty Detection", Proceedings of IEEE Conference on Computer Vision and Pattern Recognition. 2018.

SUMMARY

According to an aspect of an embodiment, a training apparatus comprising: a memory; and a processor coupled to the memory, wherein the processor is configured to: generate image data using a generator; discriminate whether the image data is real or fake by discriminator; perform training for the generator and the discriminator such that the generator maximizes a discrimination error of the discriminator and the discriminator minimizes the discrimination error; while the training is being performed, store a state of the generator that is half-trained and satisfies a pre-set condition; and retrain the discriminator by using an image generated by the half-trained generator that has the stored state.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

However, in the techniques as described above, in some cases, the capability of the discriminator to detect anomalies may be reduced. Specifically, when the discriminator is used, characteristics of the discriminator depend on data other than normal data that is erroneously generated by the generator at the end of training, so that omission of detection may increase. For example, the discriminator is expected to have the capability to discriminate a difference between normal data and an output from the generator; however, the discriminator is not able to training data that is not included in the output from the generator and not included in the normal data, so that it is impossible to expect a specific output. Meanwhile, a method using the generator needs a high detection cost, and therefore is not suitable for anomaly detection for which high-speed performance is needed.

Preferred embodiments will be explained with reference to accompanying drawings. The present invention is not limited by the embodiments below. In addition, the embodiments may be combined as appropriate as long as no contradiction is derived.

[a] First Embodiment

Description of Anomaly Detection Apparatus 10

Figure 1:
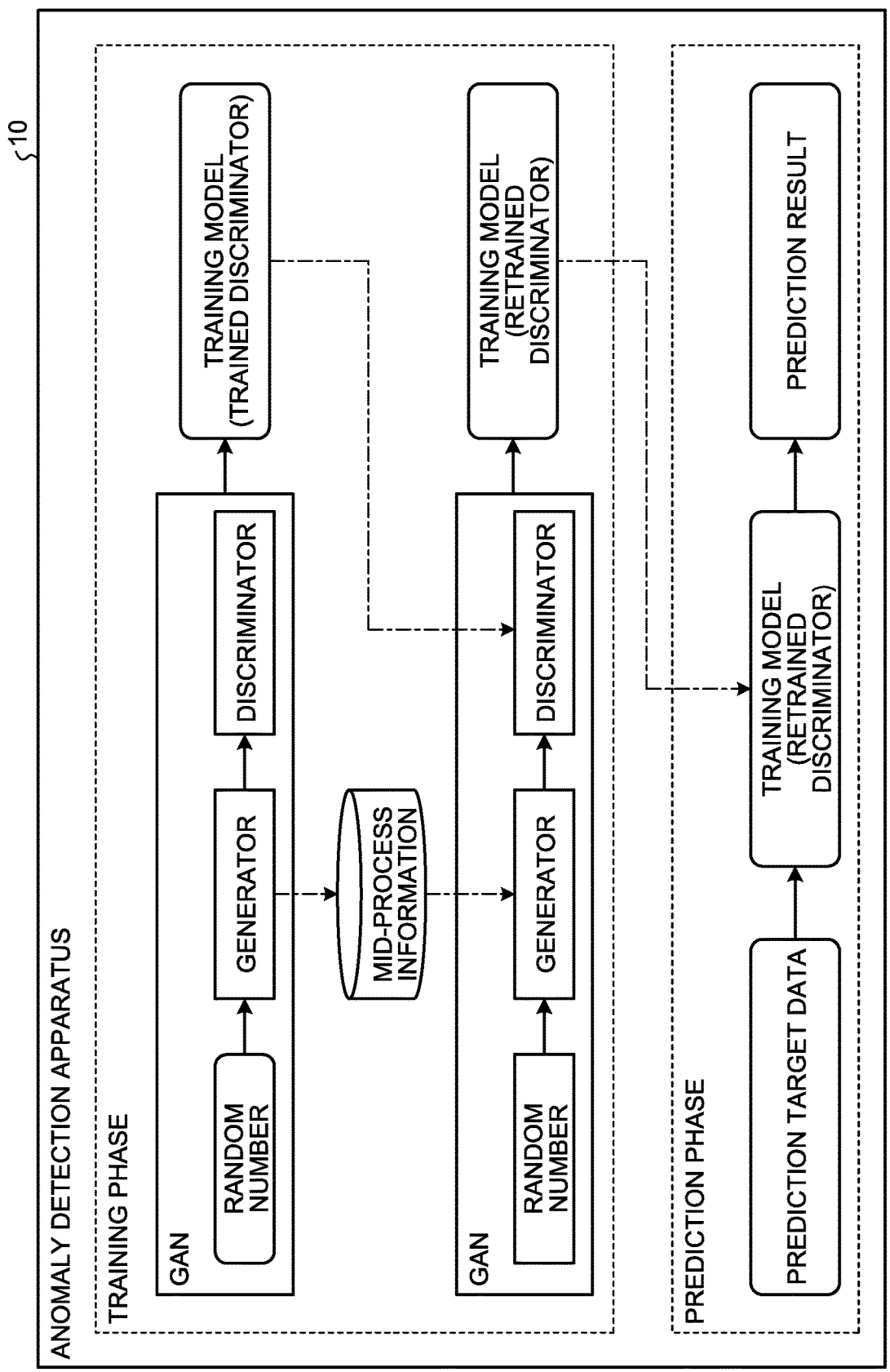
FIG. 1 is a diagram for explaining an anomaly detection apparatus according to a first embodiment.

FIG. 1 is a diagram for explaining an anomaly detection apparatus 10 according to a first embodiment. As illustrated in FIG. 1, the anomaly detection apparatus 10 is an example of a training apparatus that trains, in a training phase, a generator and a discriminator by a GAN, and performs, in a prediction phase, anomaly detection with respect to prediction target image data by using the trained discriminator.

Figure 2:
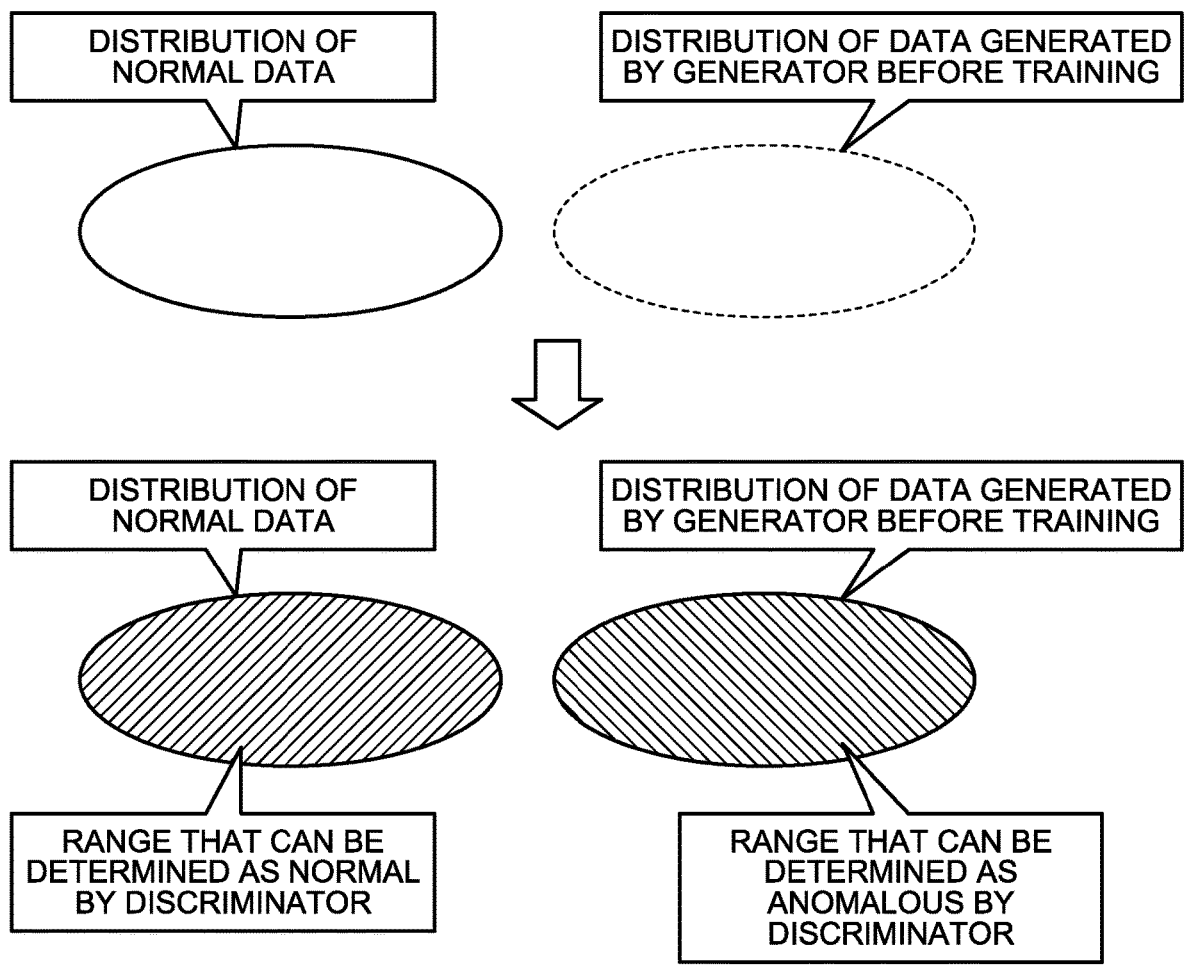
FIG. 2 is a diagram for explaining a step before training.
Figure 3:
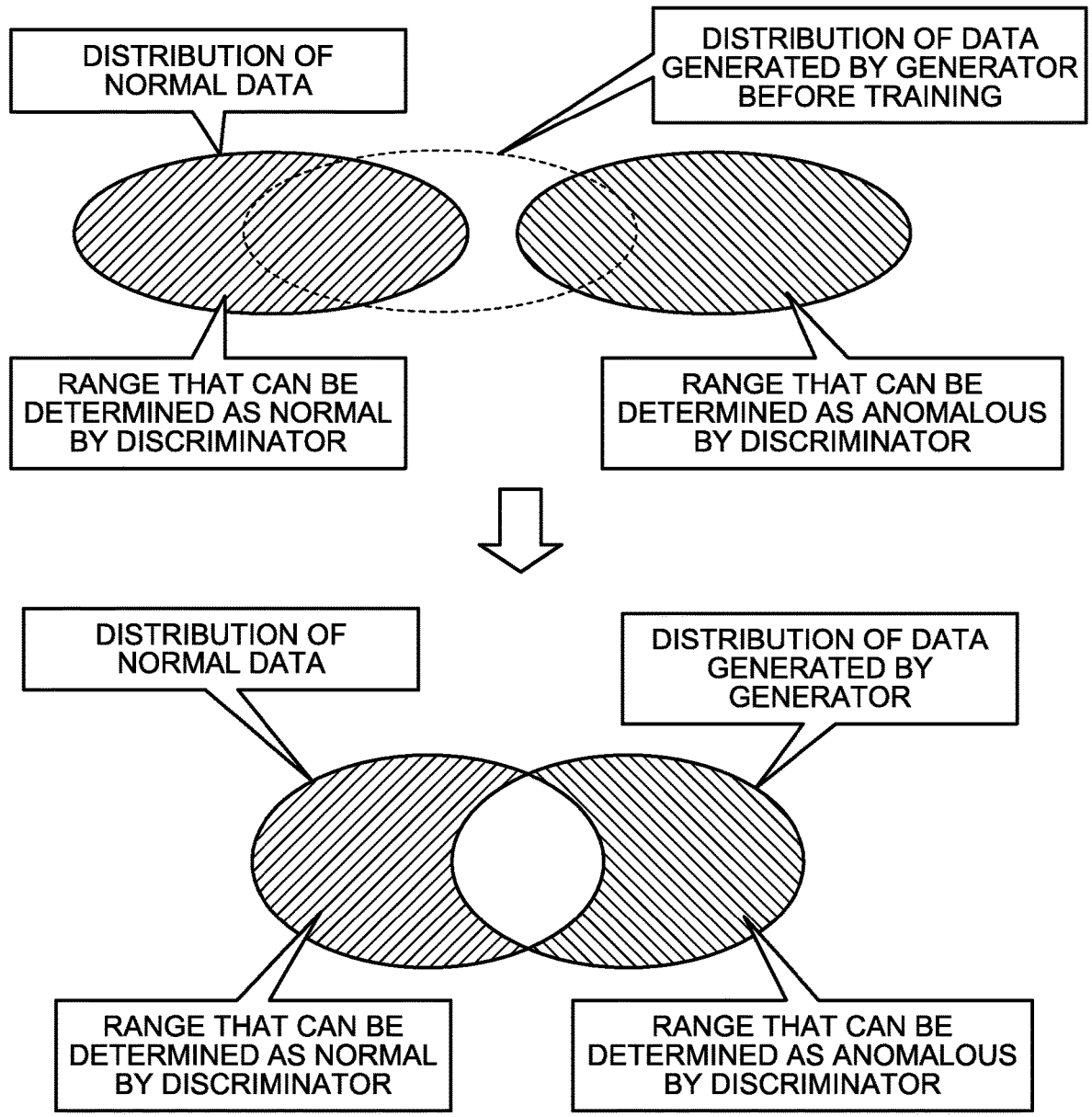
FIG. 3 is a diagram for explaining a step after start of the training.
Figure 4:
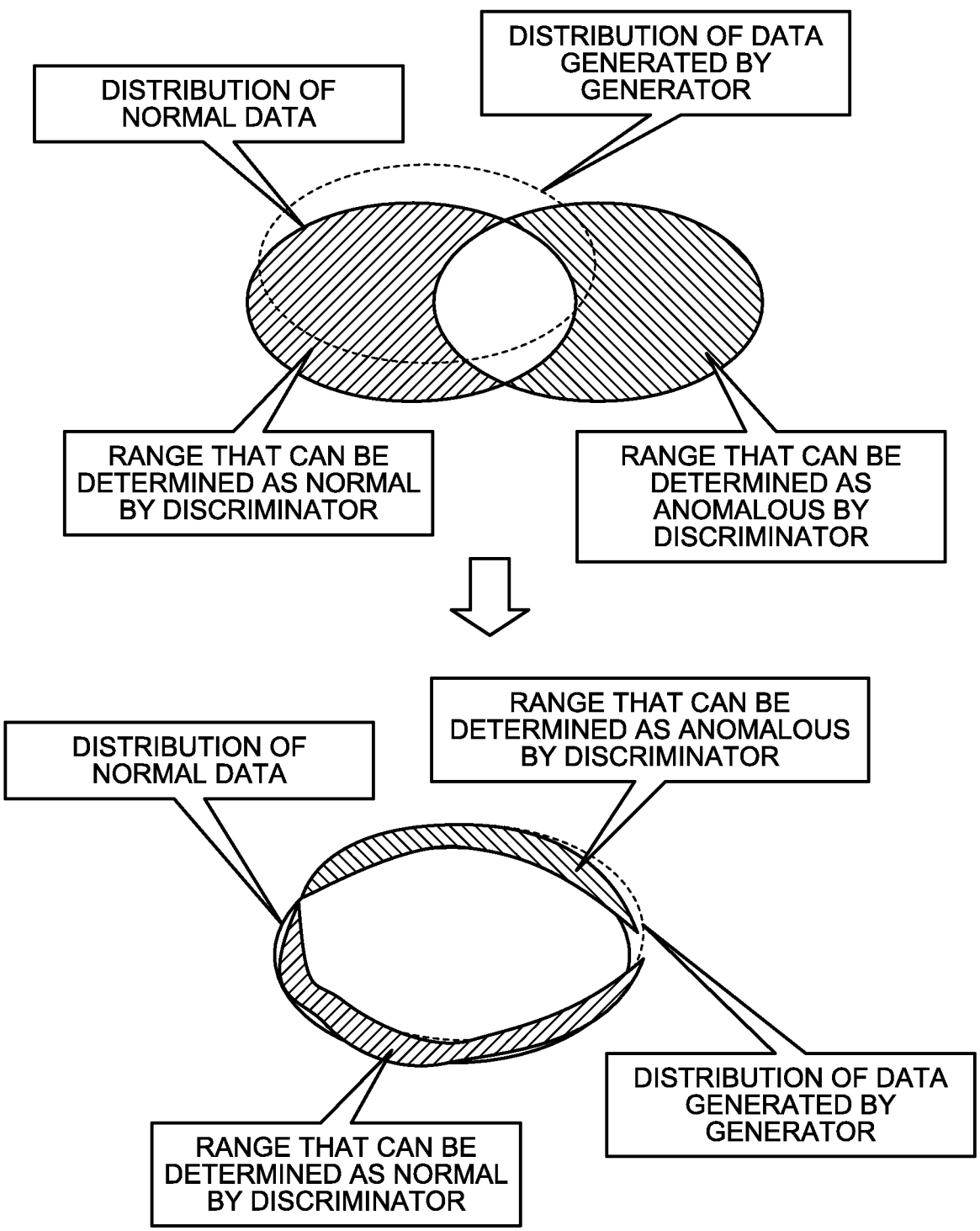
FIG. 4 is a diagram for explaining a step during the training.
Figure 5:
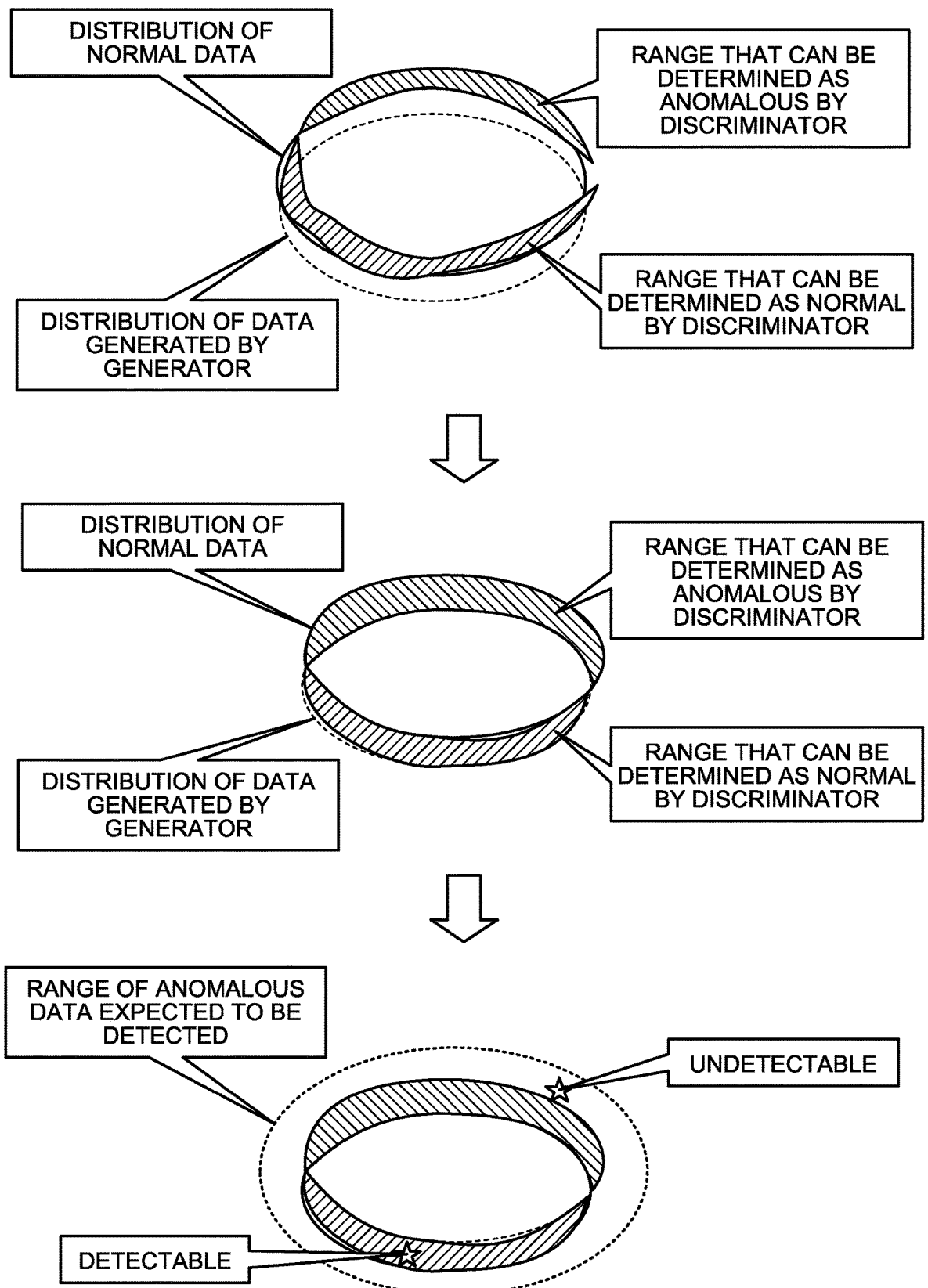
FIG. 5 is a diagram for explaining a discriminator after end of the training.

Meanwhile, in training using a general GAN, in some cases, a capability of the discriminator to detect anomalies may be reduced. A problem with the general GAN will be described below with reference to FIG. 2 to FIG. 5. In FIG. 2 to FIG. 5, with respect to the training using the general GAN, steps before start of the training, during the training, and after end of the training are illustrated. FIG. 2 is a diagram for explaining the step before the training. FIG. 3 is a diagram for explaining the step after the start of the training. FIG. 4 is a diagram for explaining the step during the training. FIG. 5 is a diagram for explaining the discriminator after the end of the training.

As illustrated in FIG. 2, before the training, the generator generates data in a different distribution from a distribution of normal data, and the discriminator trains a difference between the distribution of the normal data and the distribution of the data generated by the generator. In other words, the discriminator clearly distinguishes and discriminates between the distribution of the normal data and the distribution of the data generated by the generator.

Subsequently, as illustrated in FIG. 3, upon start of the training, training of the generator proceeds such that data to be discriminated as normal by the discriminator increases and data to be discriminated as anomalous decreases. In other words, the generator is trained to generate data that may be erroneously discriminated by the discriminator, and is thus trained such that the distribution of the data generated by the generator includes a range that can be determined as normal by the discriminator. In contrast, when the distribution of the data generated by the generator is changed with the start of the training, a probability of a discrimination result indicating that data is discriminated as normal is changed; therefore, the discriminator trains a difference between the distribution of the normal data and the distribution of the data generated by the generator.

Subsequently, when the training proceeds from the time point as illustrated in FIG. 3, as illustrated in FIG. 4, training is performed such that the distribution of the data generated by the generator includes the range that can be discriminated as normal by the discriminator in FIG. 3. In other words, the distribution of the data generated by the generator is updated so as to be largely included in the range that can be discriminated as normal by the discriminator. In contrast, the discriminator is trained to discriminate between the distribution of data generated by the updated generator and the distribution of the normal data.

When the training proceeds further, as illustrated in FIG. 5, the generator is trained to mimic data in the range that can be discriminated as normal by the discriminator in the state as illustrated in FIG. 4, to thereby cause the discriminator to make a mistake, so that the distribution of the data generated by the generator is updated so as to include the range that can be discriminated by the discriminator in FIG. 4. When the training is completed, the trained discriminator is trained to discriminate between the data generated by the generator and the normal data (real data).

However, in the general GAN, characteristics of the discriminator depend on data other than normal data that is erroneously generated by the generator at the end of training, so that omission of detection may increase. Specifically, it is possible to accurately detect an anomaly with respect to anomalous data that is present in a range that can be determined as anomalous by the trained discriminator, but it is impossible to detect anomalous data that is present outside the range. In other words, in the general GAN, in some cases, it may be difficult to train the discriminator to the same extent as a range of anomalous data that are expected to be detected.

To cope with this, the anomaly detection apparatus 10 according to the first embodiment focuses on the fact that anomalous data desired to be detected in a medical procedure does not appear at a position largely deviated from the distribution of the normal data. Further, the distribution of the data generated by the generator may temporarily deviate from the distribution of the normal data in the course of training, and therefore, the anomaly detection apparatus 10 stores half-trained generators at regular intervals and trains the discriminator by using all of the stored generators. A half-trained generator refers to a generator while it is trained.

Specifically, as illustrated in FIG. 1, the anomaly detection apparatus 10 trains the generator and the discriminator by the GAN, and acquires information on half-trained generators at regular intervals. Then, after training of the discriminator by the GAN is completed, the anomaly detection apparatus 10 retrains the trained discriminator by using each of the generators that are stored in the course of training. After completion of the retraining, the anomaly detection apparatus 10 inputs prediction target image data to the retrained discriminator and performs anomaly detection.

Functional Configuration

Figure 6:
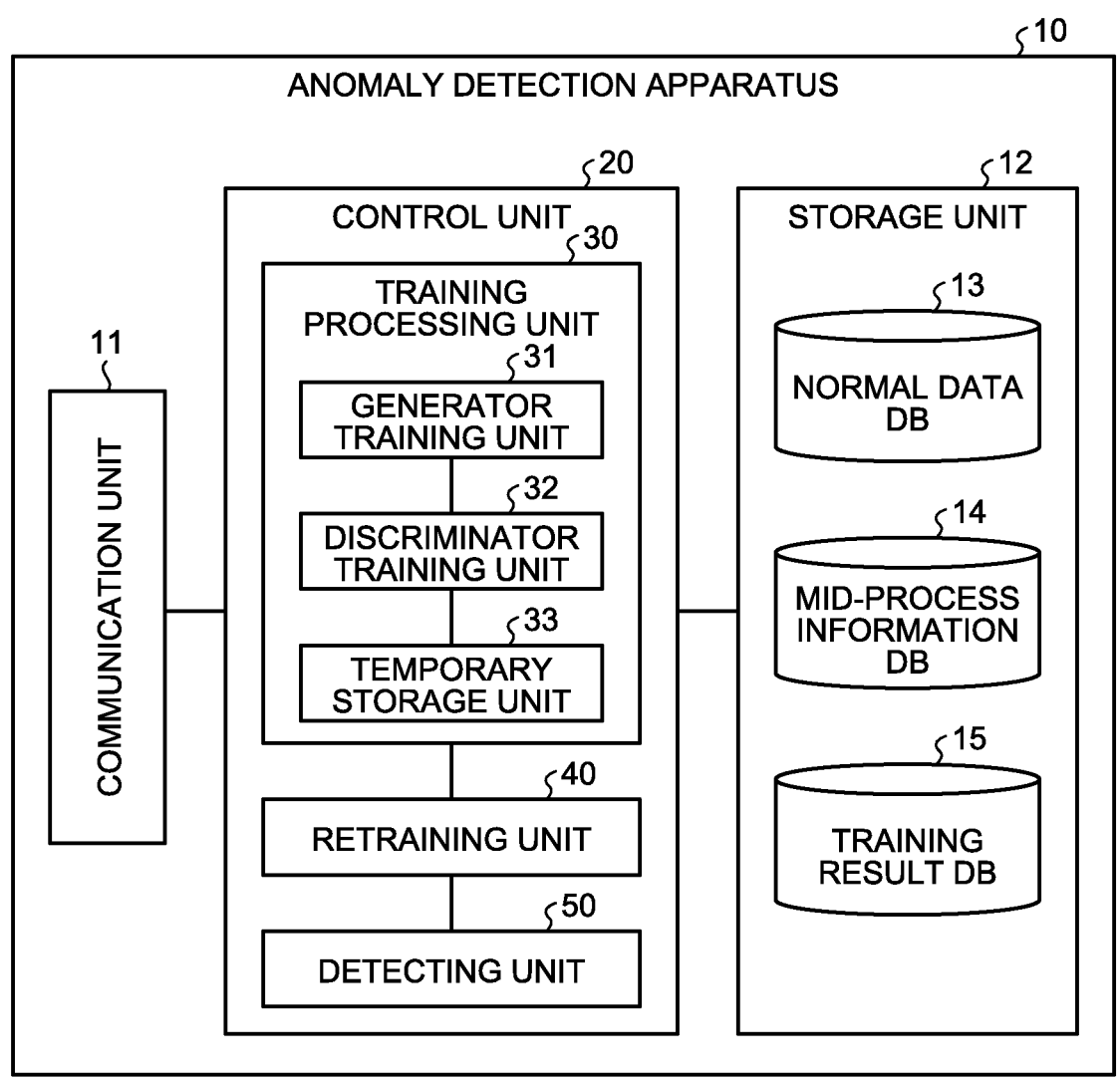
FIG. 6 is a functional block diagram illustrating a functional configuration of the anomaly detection apparatus according to the first embodiment.

FIG. 6 is a functional block diagram illustrating a functional configuration of the anomaly detection apparatus 10 according to the first embodiment. As illustrated in FIG. 6, the anomaly detection apparatus 10 includes a communication unit 11, a storage unit 12, and a control unit 20.

The communication unit 11 is a processing unit that controls communication with other apparatuses, and is, for example, a communication interface or the like. For example, the communication unit 11 receives, from an administrator terminal, an instruction to start various processes, normal data, prediction target data, and the like, and transmits, to the administrator terminal, a training result, a prediction result, and the like.

The storage unit 12 is one example of a storage device that stores therein various kinds of data and programs to be executed by the control unit 20, and is, for example, a memory, a hard disk, or the like. The storage unit 12 stores therein a normal data database (DB) 13, a mid-process information DB 14, a training result DB 15, and the like.

The normal data DP 13 is a database for storing image data that is obtained by capturing an image of an internal organ or the like in a normal state. For example, the normal data DB 13 stores therein normal data that is used in training of the discriminator by the GAN.

The mid-process information DB 14 is a database for storing information on a half-trained generator while the generator is trained by the GAN. For example, the mid-process information DB 14 stores therein various parameters, by which the half-trained generator can be reproduced (constructed), in the course of training.

The training result DB 15 is a database for storing training results of the generator and the discriminator. For example, the training result DB 15 stores therein, as training results of the generator and the discriminator using the GAN and a retraining result of the discriminator, various parameters by which it is possible to generate the trained generator and the trained discriminator for each of which training is completed.

The control unit 20 is a processing unit that controls the entire anomaly detection apparatus 10, and is, for example, a processor or the like. The control unit 20 includes a training processing unit 30, a retraining unit 40, and a detecting unit 50, trains a discriminator with high discrimination accuracy, and performs anomaly detection with respect to input prediction target image data.

The training processing unit 30 is a processing unit that includes a generator training unit 31, a discriminator training unit 32, and a temporary storage unit 33, and trains the generator and the discriminator using the GAN.

The generator training unit 31 is a processing unit that trains the generator of the GAN. Specifically, similarly to the general GAN, the generator training unit 31 trains the generator such that data to be determined as normal by the discriminator increases and data to be determined as anomalous decreases. In other words, the generator is trained to maximize a discrimination error of the discriminator.

For example, the generator training unit 31 causes the generator to generate image data by using a latent variable that is a random number, random noise, or the like, and that is what is called a seed. Then, the generator training unit 31 inputs the generated image data (hereinafter, may be described as generated data) to the discriminator and acquires a discrimination result of the discriminator. Then, the generator training unit 31 trains the generator by using the discrimination result such that the generated data can be discriminated as normal data by the discriminator.

In other words, the generator training unit 31 trains the generator such that the distribution of the generated data that is generated by the generator matches the distribution of the normal data. If training is completed, the generator training unit 31 stores information on the trained generator in the training result DB 15.

The discriminator training unit 32 is a processing unit that trains the discriminator of the GAN. Specifically, similarly to the general GAN, the discriminator training unit 32 trains the discriminator such that the discriminator is able to distinguish between the normal data stored in the normal data DB 13 and the generated data generated by the generator. In other words, the discriminator is trained to minimize the discrimination error.

For example, the discriminator training unit 32 acquires the generated data from the generator, inputs the generated data to the discriminator, and acquires an output result of the discriminator. Then, the discriminator training unit 32 trains the discriminator such that, regarding a probability of normality indicating the normal data included in the output result and a probability of anomaly indicating the generated data, the probability of anomaly increases and the probability of normality decreases.

In other words, the discriminator training unit 32 causes the discriminator to train a difference between the distribution of the generated data generated by the generator and the distribution of the normal data. If training is completed, the discriminator training unit 32 stores information on the trained discriminator in the training result DB 15.

The temporary storage unit 33 is a processing unit for storing a half-trained generator. For example, while the generator is being trained by the generator training unit 31, the temporary storage unit 33 acquires various parameters indicating a state of the half-trained generator from the generator at regular time intervals or every time a predetermined number of times of training is performed, and stores the various parameters in the mid-process information DB 14.

The retraining unit 40 is a processing unit that retrains the discriminator that has been trained by the GAN. Specifically, the retraining unit 40 retrains the discriminator by using all of half-trained generators that are stored in the temporary storage unit 33.

For example, if the training processing unit 30 completes training, the retraining unit 40 reads, from the mid-process information DB 14, information, such as parameters, and generates each of the half-trained generators. Similarly, the retraining unit 40 reads a parameter or the like of the discriminator from the training result DB 15 and generates the trained discriminator.

Here, it is assumed that four half-trained generator are generated. In this case, the retraining unit 40 generates generated data by using the first generator, inputs the generated data to the trained discriminator, and trains the discriminator. Subsequently, the retraining unit 40 constructs generated data by using the second generator, inputs the generated data to the discriminator trained with the first generator, and trains the discriminator. In this manner, the retraining unit 40 retrains the discriminator by sequentially using each of the half-trained generators. Then, if retraining is completed, the retraining unit 40 stores information on the retrained discriminator in the training result DB 15.

The detecting unit 50 is a processing unit that detects an anomaly from input image data. For example, if the retraining unit 40 completes retraining, the detecting unit 50 reads a parameter or the like related to the retrained discriminator from the training result DB 15 and constructs the discriminator. Then, upon receiving prediction target image data, the detecting unit 50 inputs the image data to the constructed discriminator and obtains an output result.

Here, as for the probability of normality indicating the normal data included in the output result and the probability of anomaly indicating the generated data, if the probability of normality is higher, the detecting unit 50 discriminates the input image data as normal image data, and if the probability of anomaly is higher, the detecting unit 50 discriminates the input image data as anomalous image data. Then, the detecting unit 50 transmits a discrimination result to the administrator terminal, displays the discrimination result on a display unit, such as a display, or stores the discrimination result in the storage unit 12.

Figure 7:
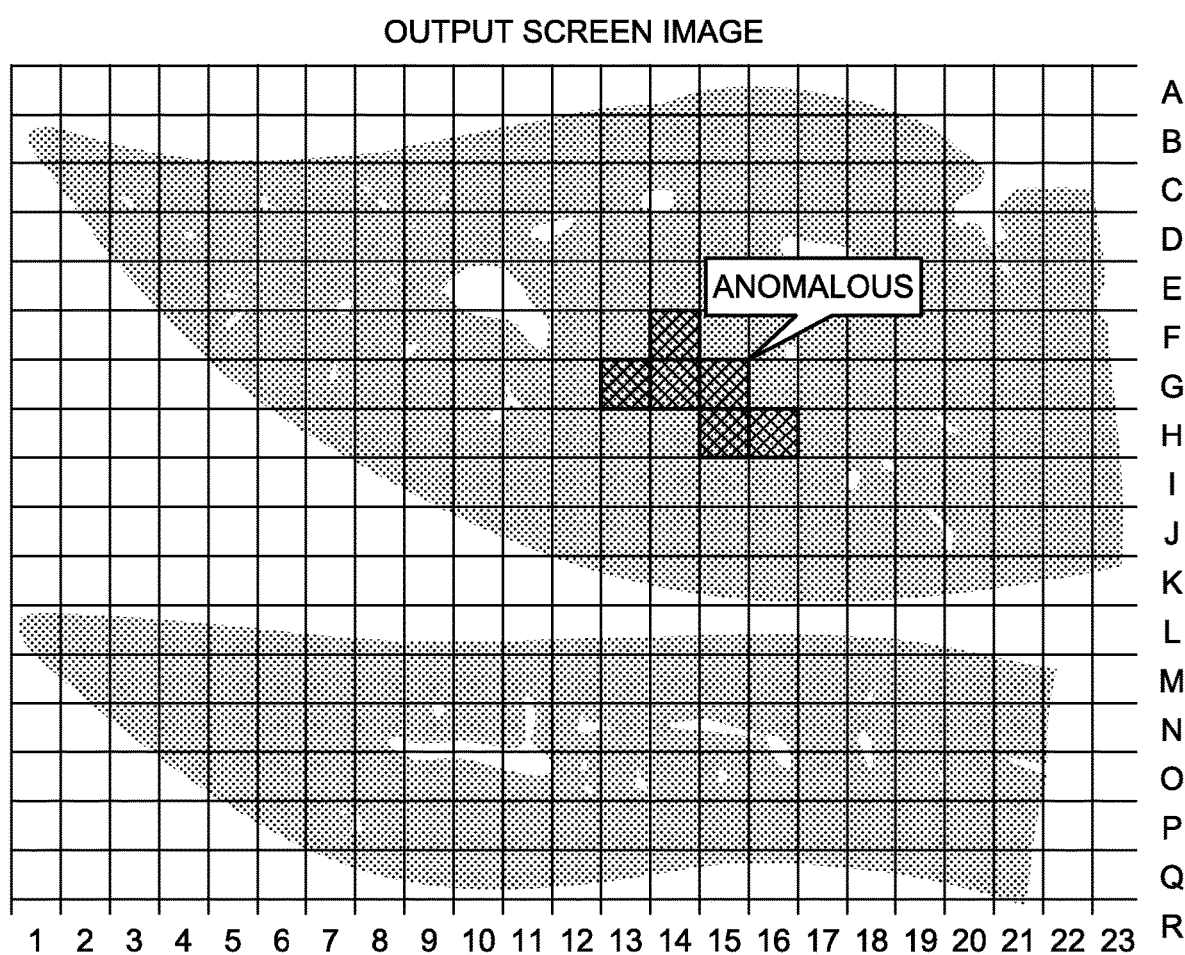
FIG. 7 is a diagram for explaining an example of a detection result.

FIG. 7 is a diagram for explaining an example of a detection result. As illustrated in FIG. 7, the detecting unit 50 first divides an input image that is a prediction target into small regions, thereafter inputs the image data to the discriminator trained by the retraining unit 40, and acquires a discrimination result. Then, the detecting unit 50 is able to provide a user with regions that are determined as anomalous by the discriminator.

Flow of Training Process

Figure 8:
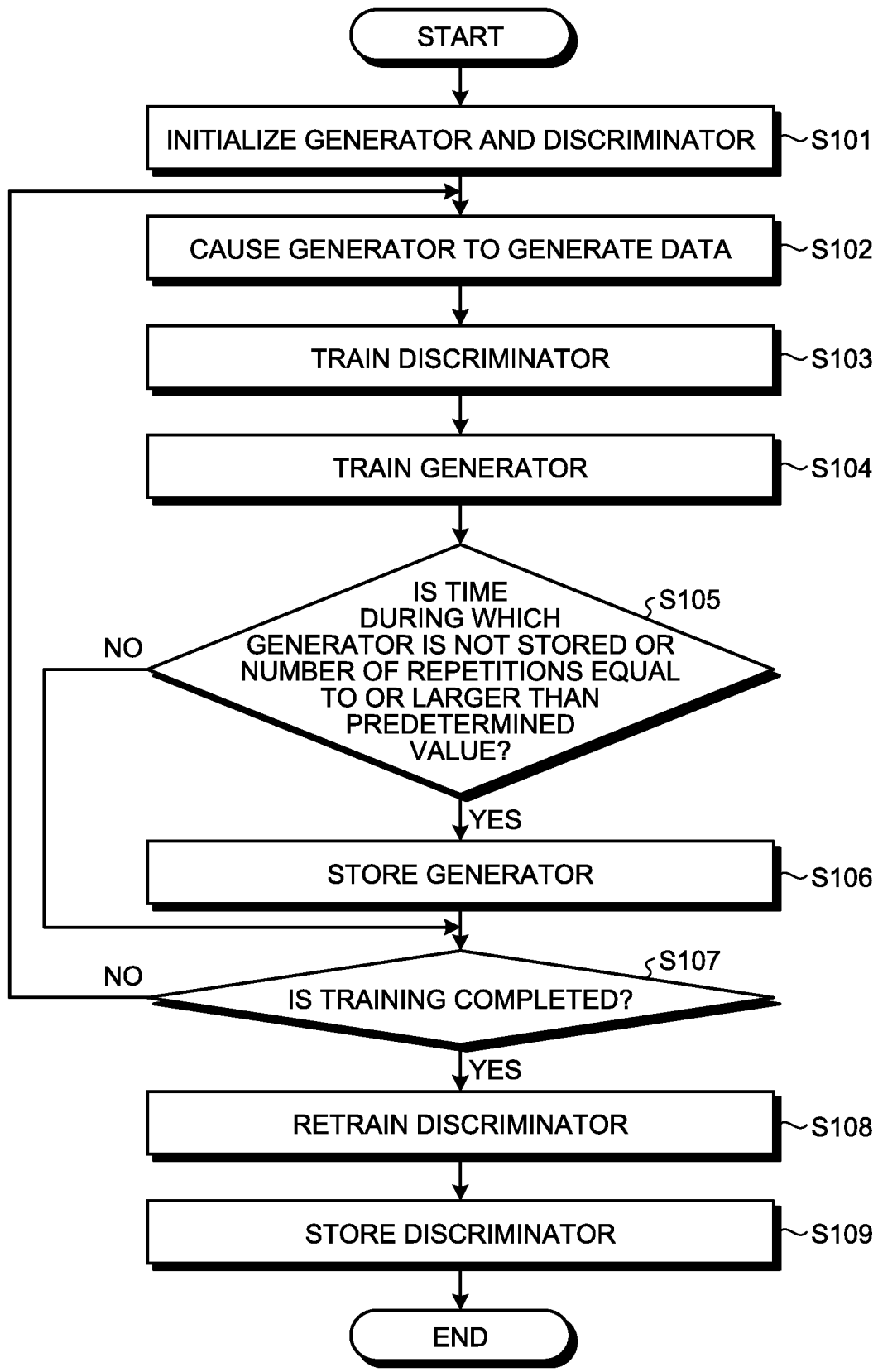
FIG. 8 is a flowchart illustrating the flow of a training process according to the first embodiment.

FIG. 8 is a flowchart illustrating the flow of the training process according to the first embodiment. As illustrated in FIG. 8, if an instruction on the training process is issued, the training processing unit 30 initializes the generator and the discriminator (S101).

Subsequently, the generator training unit 31 causes the generator to generate data (generated data) (S102), and the discriminator training unit 32 trains the discriminator such that the discriminator is able to distinguish between normal data and the generated data (S103). Then, the generator training unit 31 trains the generator such that the generated data can be discriminated as normal data by the discriminator (S104).

Thereafter, if a time during which the generator is not stored or the number of repetitions (the number of times of training) is equal to or larger than a predetermined value (S105: Yes), the temporary storage unit 33 stores therein the half-trained generator (S106). If the time during which the generator is not stored or the number of repetitions is smaller than the predetermined value (S105: No), a process at S107 is performed without performing the process at S106.

Thereafter, until the training is completed (S107: No), the processes from S102 are repeated. In contrast, if the training is completed (S107: Yes), the retraining unit 40 retrains the discriminator such that the discriminator is able to discriminate between the normal data and data (generated data) generated by the stored generator (S108). If retraining is completed, the retraining unit 40 stores the discriminator (S109).

Flow of Detecting Process

Figure 9:
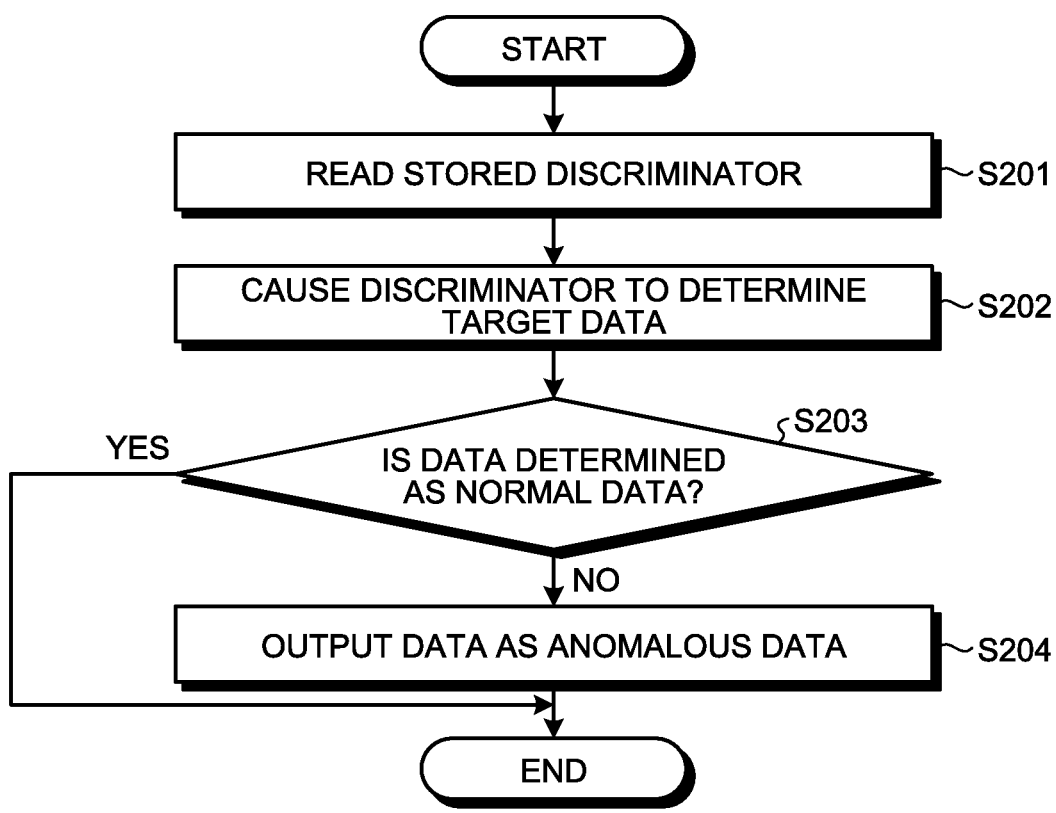
FIG. 9 is a flowchart illustrating the flow of a detecting process according to the first embodiment.

FIG. 9 is a flowchart illustrating the flow of a detecting process according to the first embodiment. As illustrated in FIG. 9, if an instruction on the detecting process is issued, the detecting unit 50 reads the stored discriminator (S201). Subsequently, the detecting unit 50 inputs target data to the discriminator and determines (discriminates) whether the target data is anomalous (S202).

If the detecting unit 50 determines that the target data is normal (S203: Yes), the detecting unit 50 terminates the process. If the detecting unit 50 does not determine that the target data is normal (S203: No), the detecting unit 50 outputs the target data as anomalous data (S204).

Effects

As described above, the anomaly detection apparatus 10 focuses on the fact that, for example, anomalous data desired to be detected in a medical procedure does not appear at a position largely deviated from the distribution of the normal data, and retrains the discriminator by using the half-trained generators. As a result, the anomaly detection apparatus 10 is able to retrain the discriminator by using the generators capable of exhaustively generating anomalous data that are expected to be present around normal data. Therefore, it is possible to extend a discrimination range of the discriminator.

Figure 10:
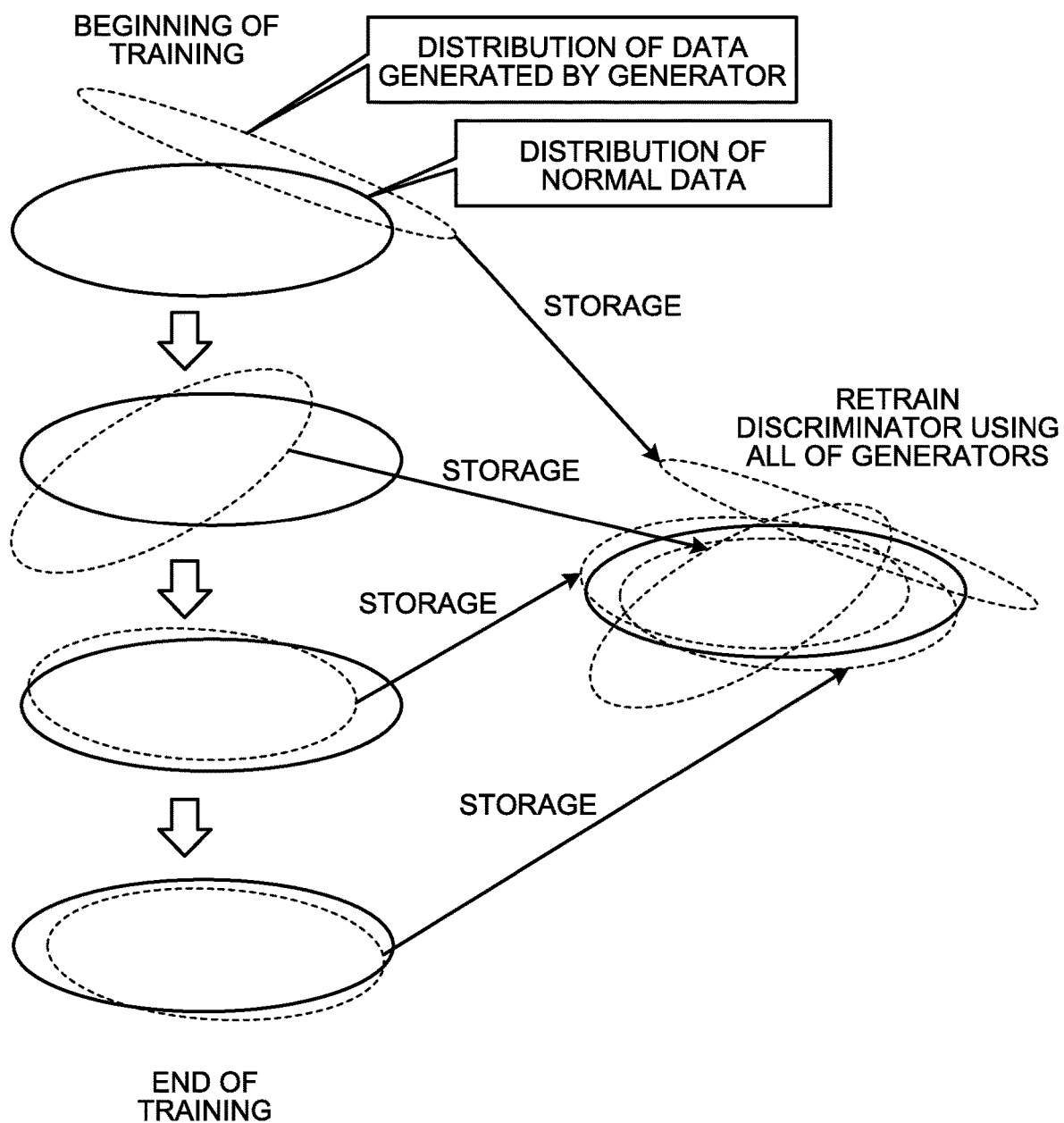
FIG. 10 is a diagram for explaining temporary storage and retraining.

FIG. 10 is a diagram for explaining temporary storage and retraining. Storing the half-trained generators is to store states of the half-trained generators and to store distributions of generated data generated by the half-trained generators such that the distributions match the distribution of the normal data. In other words, as illustrated in FIG. 10, it is possible to store the process of training the distribution of each piece of generated data generated by the generators from the beginning of the training to the end of the training. Therefore, by performing retraining by using all of the stored generators, it is possible to train each of the distributions of each piece of the generated data that is generated by each of the generators, so that it is possible to train a range that is not covered by the discriminator that has been trained by the GAN.

Figure 11:
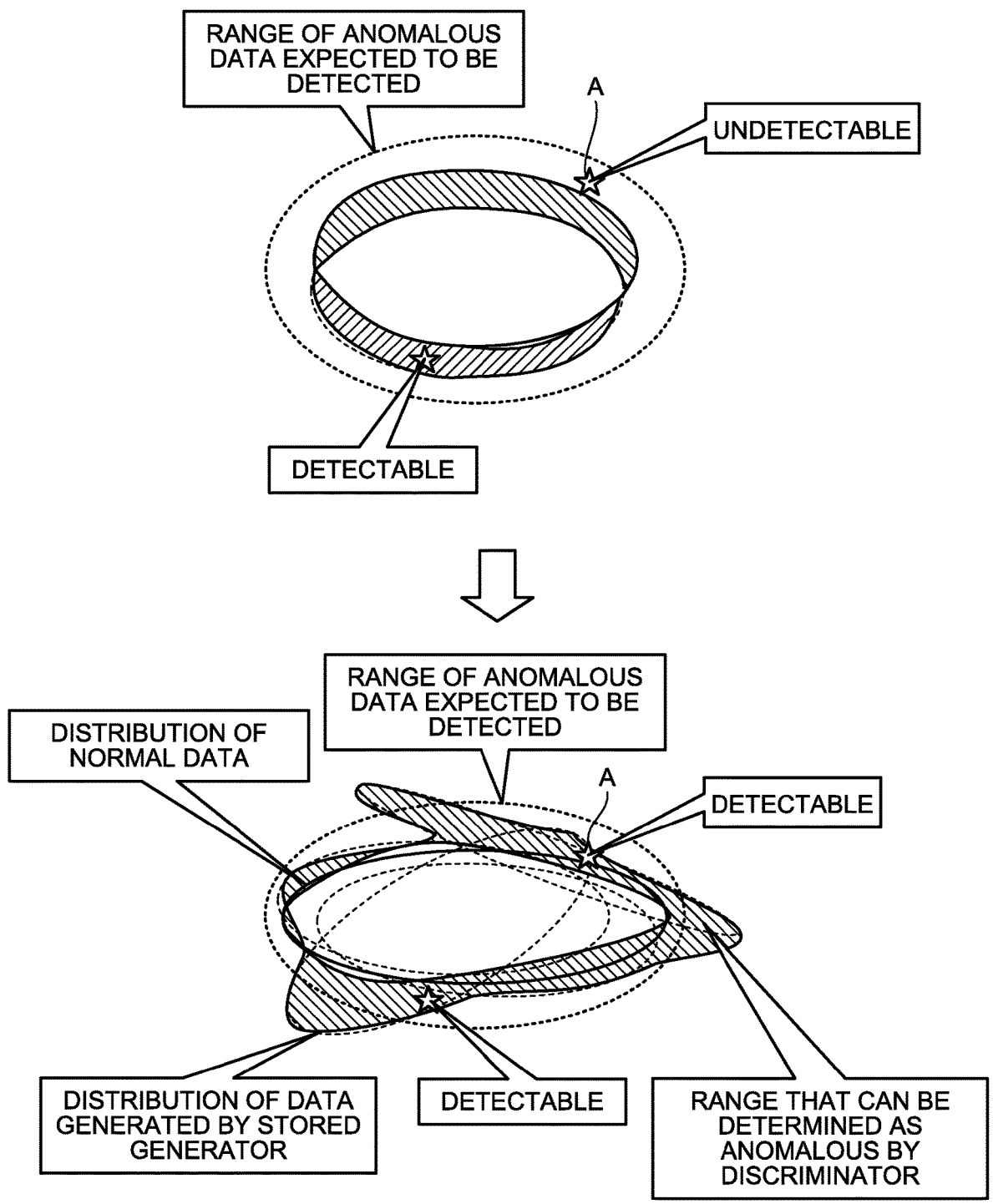
FIG. 11 is a diagram for explaining effects.

FIG. 11 is a diagram for explaining effects. As illustrated in FIG. 11, in the general GAN, characteristics of the discriminator depend on data other than normal data that is erroneously generated by the generator at the end of training, so that it is difficult to train the discriminator so as to cover a range in which anomalies are expected to be detected, and omission of detection frequently occurs. In the example illustrated in FIG. 11, the discriminator is not able to detect, as anomalous, data A located outside a range of a data distribution of the generator.

In contrast, in the training of the discriminator according to the first embodiment, it is possible to retrain the distributions of the generated data generated by the generators that are stored in the course of training, so that it is possible to cover larger areas around the normal data without depending on the state of the completely-trained generator. As a result, the retrained discriminator is able to detect the data A, which has not been detected by the discriminator of the general GAN, as anomalous data.

[b] Second Embodiment

In the first embodiment, the example has been described in which the half-trained generators are stored at regular intervals, but it may be possible to improve the performance of the discriminator by controlling an interval for storage instead of adopting regular intervals. Therefore, in a second embodiment, an example will foe described in which the generator is stored not at regular intervals but at a timing at which a loss of the discriminator decreases to below a threshold again after the loss temporarily rises to the threshold or higher.

Figure 12:
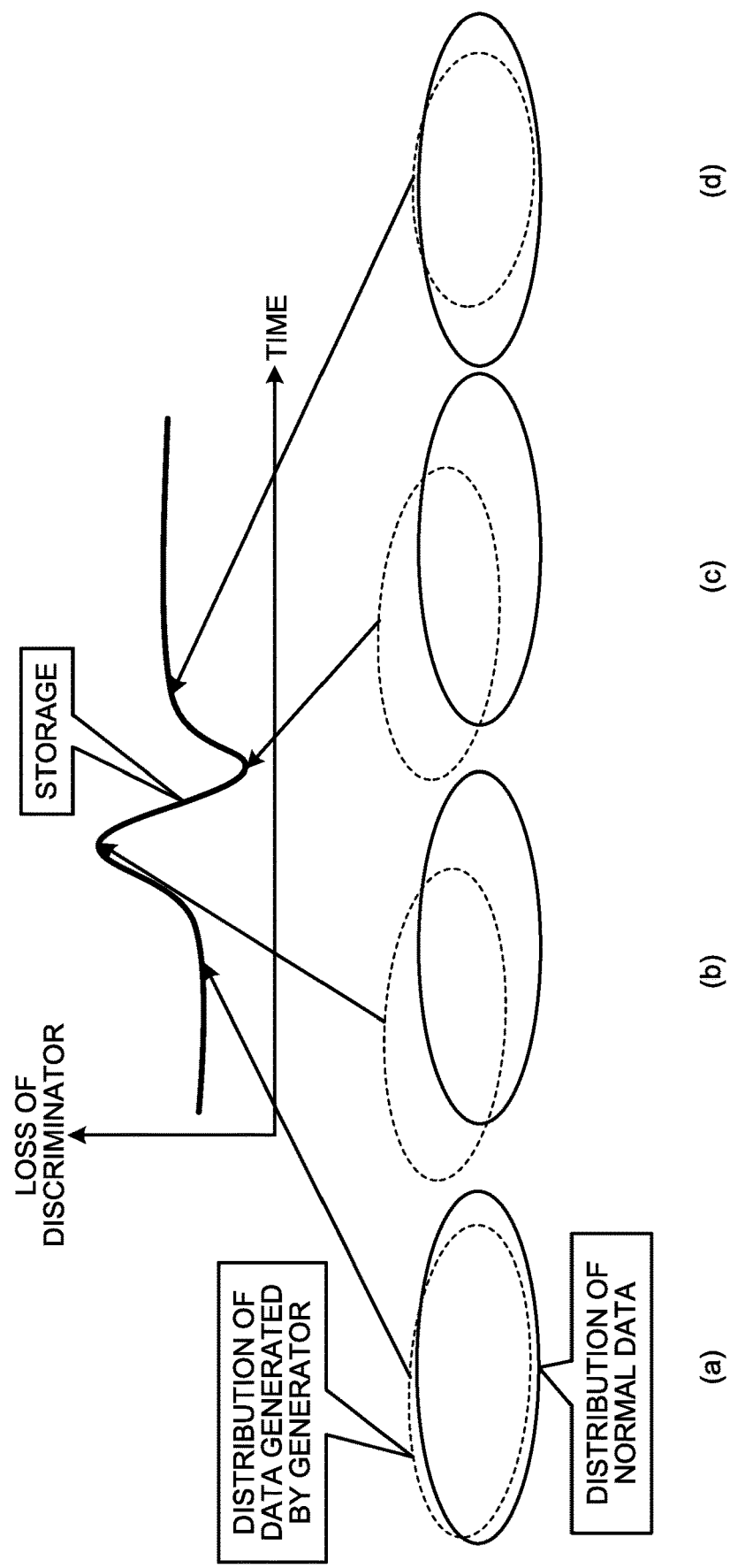
FIG. 12 is a diagram for explaining a training process according to a second embodiment.

FIG. 12 is a diagram for explaining a training process according to the second embodiment. In FIG. 12, a temporal change of a loss of the discriminator, in other words, a temporal change of a rate at which discrimination by the discriminator is unsuccessful in training based on the GAN is illustrated. As illustrated in FIG. 12, when training of the generator by the GAN proceeds, the distribution of the data generated by the generator deviates to a region that is not covered by the discriminator (FIG. 12(a)), and a loss of the discriminator increases (FIG. 12(b)). Thereafter, training of the discriminator proceeds, and the discriminator follows the trained generator, so that the loss of the discriminator decreases (FIG. 12(c)), and the deviation is eliminated (FIG. 12(d)).

Therefore, the temporary storage unit 33 stores therein the state of the generator when the loss of the discriminator increases and thereafter starts to decrease. Meanwhile, if the temporary storage unit 33 is to store a plurality of generators at this timing, it may be possible to store the generators at regular time intervals from the start of decrease of the loss of the discriminator. With this configuration, it is possible to store a time point at which a difference between the distribution of the data generated by the generator and the distribution of the normal data is large, so that it is possible to extend a range that can be trained by the discriminator. Consequently, it is possible to improve the performance of the discriminator.

Figure 13:
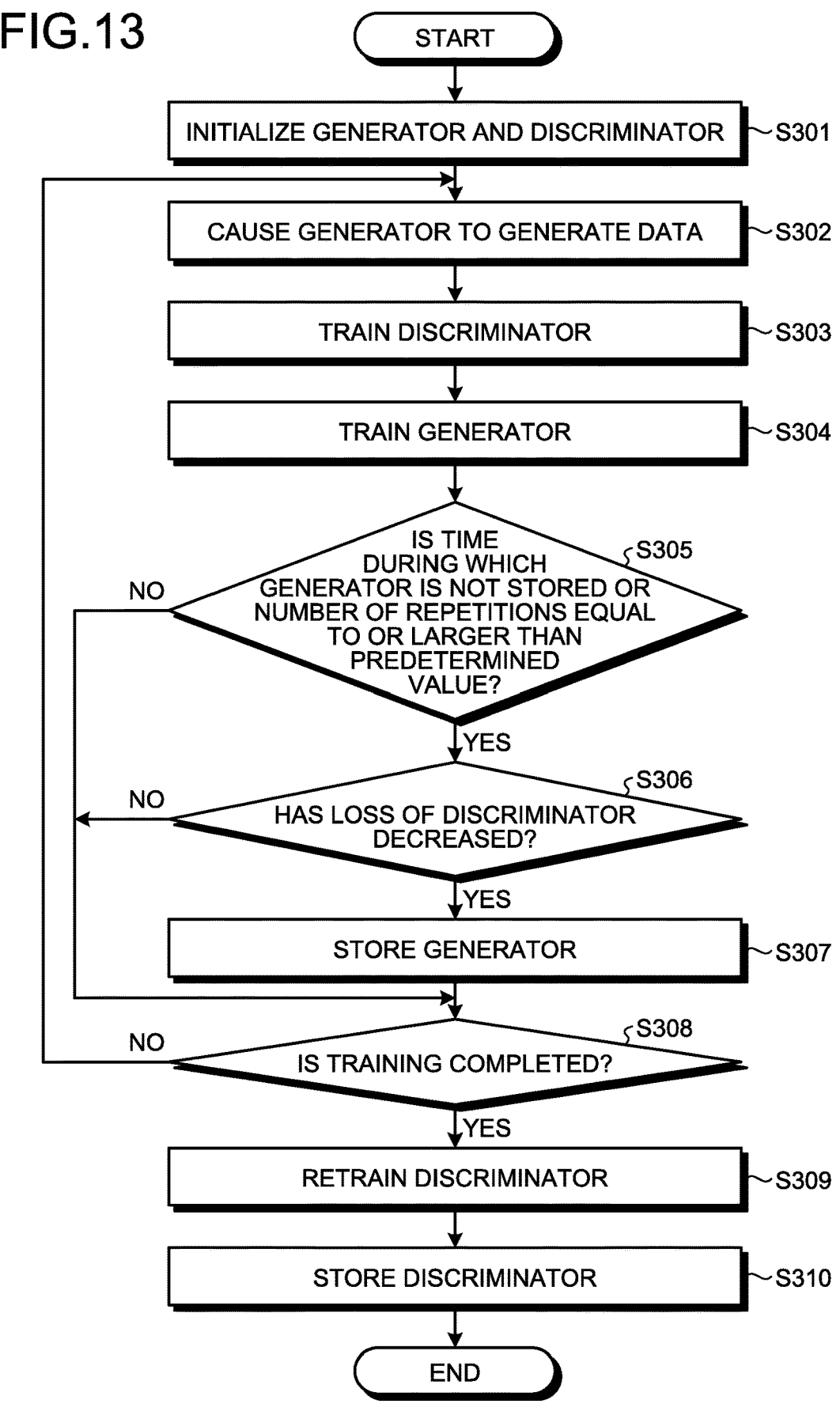
FIG. 13 is a flowchart illustrating the flow of the training process according to the second embodiment.

FIG. 13 is a flowchart illustrating the flow of the training process according to the second embodiment. As illustrated in FIG. 13, if an instruction on the training process is issued, the training processing unit 30 initializes the generator and the discriminator (S301).

Subsequently, the generator training unit 31 causes the generator to generate data (generated data) (S302), and the discriminator training unit 32 trains the discriminator such that the discriminator is able to distinguish between the normal data and the generated data (S303). Then, the generator training unit 31 trains the generator such that the generated data can be discriminated as normal data by the discriminator (S304).

Thereafter, if a time during which the generator is not stored or the number of repetitions is equal to or larger than a predetermined value (S305: Yes), and if the loss of the discriminator has decreased (S306: Yes), the temporary storage unit 33 stores therein the half-trained generator (S307). If the time during which the generator is not stored or the number of repetitions is smaller than the predetermined value (S305: No), or if the loss of the discriminator has not decreased (S306: No), a process at S308 is performed without performing the process at S307.

Thereafter, until the training is completed (S308: No), the processes from S302 are repeated. In contrast, if the training is completed (S308: Yes), the retraining unit 40 retrains the discriminator such that the discriminator is able to discriminate between the normal data and data (generated data) generated by the stored generator (S309). If retraining is completed, the retraining unit 40 stores the discriminator (S310). A detecting process is the same as that of the first embodiment, and therefore, detailed explanation thereof will be omitted.

[c] Third Embodiment

In the second embodiment, when the generator starts to generate anomalous data, the discriminator immediately follows the generator; therefore, a range of deviation of the distribution of the generated data generated by the generator in a region that is not covered by the discriminator is limited, and it is difficult to determine a degree of progress of the deviation.

Therefore, in a third embodiment, two discriminators for which different training speeds are set are used, and a generator in a state in which a deviation has progressed is accurately stored, to thereby improve the performance of the discriminators. Specifically, the generator is trained using a low-speed discriminator, and the degree of progress of the deviation is measured using a high-speed discriminator. In the third embodiment, a percentage of generated data that can be discriminated as the generated data by the high-speed discriminator is used as an index. Further, if the deviation progresses to a certain degree or higher, the generator is stored and the high-speed discriminator is copied to the low-speed discriminator so as to prevent further progress of the deviation.

Figure 14:
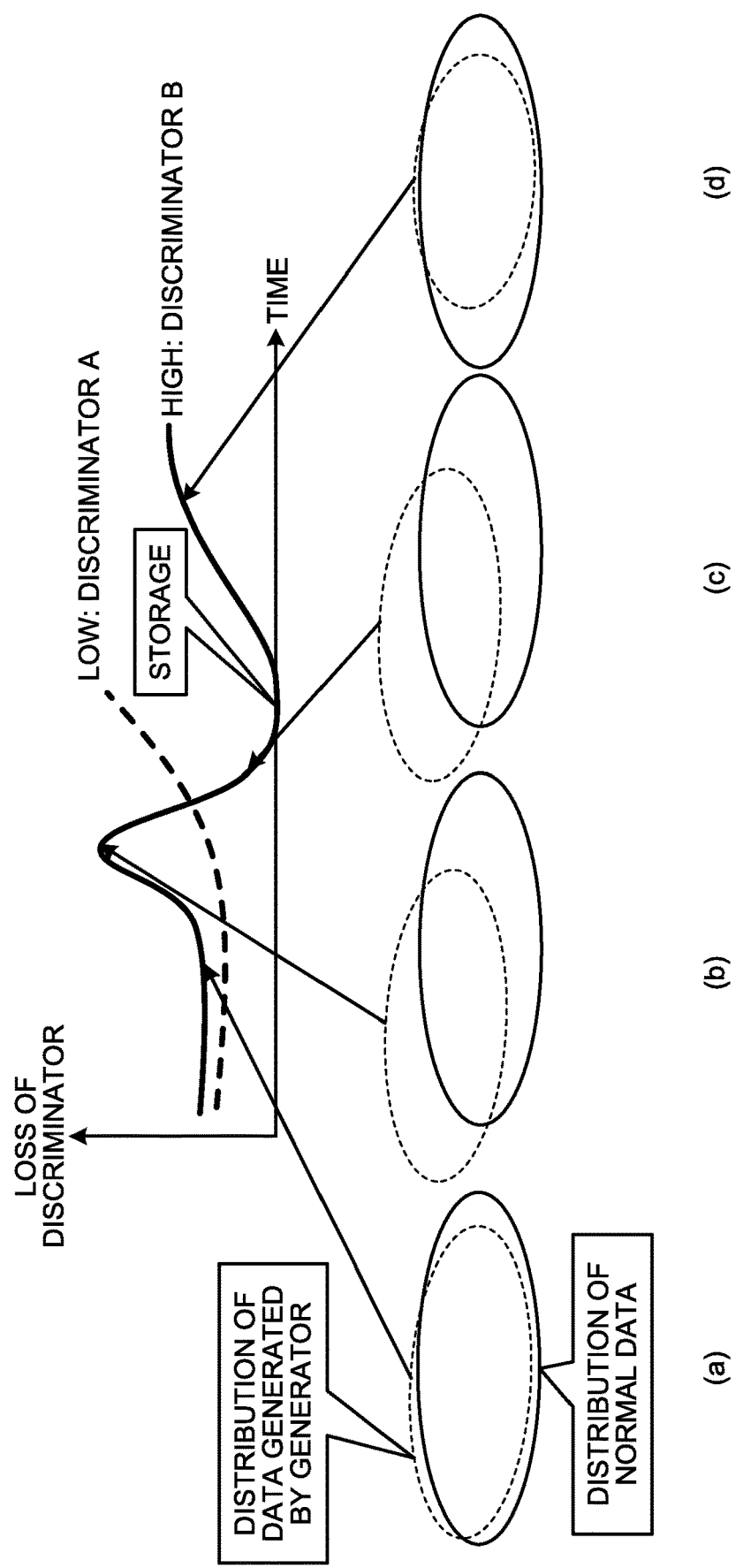
FIG. 14 is a diagram for explaining a training process according to a third embodiment.

FIG. 14 is a diagram for explaining a training process according to the third embodiment. As illustrated in FIG. 14, FIG. 14 illustrates a temporal change of a loss of each of the discriminators in training based on the GAN using two discriminators, such as a discriminator A for which a low training speed is set (hereinafter, may be described as the discriminator A or the low-speed discriminator A) and a discriminator B for which a high training speed is set (hereinafter, may be described as the discriminator B or the high-speed discriminator B).

As illustrated in FIG. 14, when training of the generator by the GAN proceeds, the distribution of the data generated by the generator starts to deviate to a region that is not covered by the high-speed discriminator B (FIG. 14(a)), and the loss of the high-speed discriminator B increases (FIG. 14(b)). However, because the training speed of the low-speed discriminator A is low, an increase in the loss of the low-speed discriminator A is smaller than that of the high-speed discriminator B.

Thereafter, training of both of the discriminators proceeds, in particular, training of the high-speed discriminator B proceeds and follows the training of the generator, so that the loss of the high-speed discriminator B decreases while the low-speed discriminator A is not able to allow for deviation (FIG. 14(c)). In other words, the low-speed discriminator A is not able to follow the training of the generator, so that correction of discrimination does not proceed.

At this time, the temporary storage unit 33 stores therein the half-trained generator. In other words, when the deviation of the high-speed discriminator B progresses to a certain level or higher, the temporary storage unit 33 stores therein the generator that is trained using the low-speed discriminator A. In other words, the temporary storage unit 33 stores therein the state of the generator when the loss of the high-speed discriminator A increases and thereafter starts to decrease and when the loss of the low-speed discriminator B increases. As a threshold for determining whether the loss is equal to or larger than a predetermined value, it may be possible to use an identical value for the discriminator A and the discriminator B.

Then, the temporary storage unit 33 copies a parameter, such as a weight, of the high-speed discriminator to the low-speed discriminator A, and resumes training at the two training speeds (FIG. 14(d)). In other words, both of the two discriminators are modified to have the states of the high-speed discriminators, and low-speed training and high-speed training are performed from the modified states.

In this manner, if the training using the two discriminators is completed, the retraining unit 40 retrains the discriminator B using the temporarily-stored half-trained generator.

Figure 15:
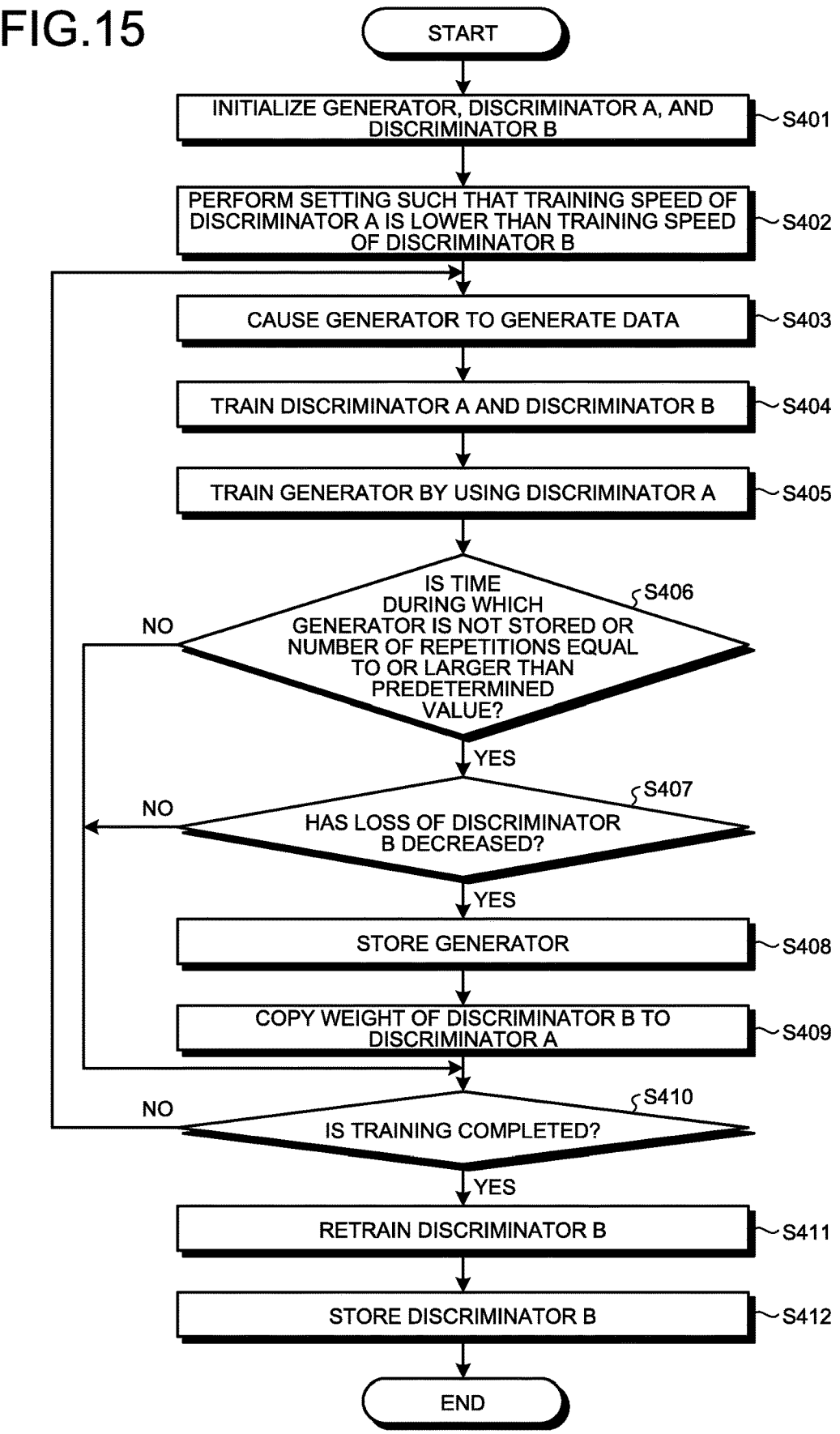
FIG. 15 is a flowchart illustrating the flow of the training process according to the third embodiment.

FIG. 15 is a flowchart illustrating the flow of the training process according to the third embodiment. As illustrated in FIG. 15, if an instruction on the training process is issued, the training processing unit 30 initializes the generator, the discriminator A, and the discriminator B (S401).

Subsequently, the generator training unit 31 performs setting such that the training speed of the discriminator A is lower than the training speed of the discriminator B (S402). For example, the generator training unit 31 decreases the training speed by reducing a training rate or a training frequency.

Then, the generator training unit 31 causes the generator to generate data (generated data) (S403), and the discriminator training unit 32 trains the discriminator A and the discriminator B such that the discriminators are able to distinguish between the normal data and the generated data (S404). Subsequently, the generator training unit 31 trains the generator such that the generated data can be discriminated as normal data by the discriminator A (S405).

Thereafter, if a time during which the generator is not stored or the number of repetitions is equal to or larger than a predetermined value, (S406: Yes), and if the loss of the discriminator B has decreased (S407: Yes), the temporary storage unit 33 stores therein the half-trained generator (S408). Subsequently, the temporary storage unit 33 copies a parameter, such as a weight, of the discriminator B to the discriminator A (S409).

If the time during which the generator is not stored or the number of repetitions is smaller than the predetermined value (S406: No), or if the loss of the discriminator has not decreased (S407: No), a process at S410 is performed without performing the processes at S408 and S409.

Thereafter, until the training is completed (S410: No), the processes from S403 are repeated. In contrast, if the training is completed (S410: Yes), the retraining unit 40 retrains the discriminator B such that the discriminator is able to discriminate between the normal data and data (generated data) generated by the stored generator (S411). If retraining is completed, the retraining unit 40 stores the discriminator B (S412). A detecting process is the same as that of the first embodiment, and therefore, detailed explanation thereof will be omitted.

[d] Fourth Embodiment

While the embodiments of the present invention have been described above, the present invention may be embodied in various forms other than the above-described embodiments.

Training

For example, a timing to terminate the training process can be set to an arbitrarily time point, such as a time point at which training using a predetermined number or more of pieces of training data is completed or a time point at which the loss of the discriminator decreases to below a threshold. Further, the technique can be applied to various fields in which it is determined whether unauthorized invasion has occurred or hazardous materials are brought in, in addition to application to medical image data.

Timing of Retraining

In the embodiments as described above, the example has been described in which the discriminator is retrained after training is completed, but embodiments are not limited to this example. For example, the discriminator may be simultaneously trained by a process using the normal GAN and by a process using the temporarily-stored half-trained generator. In other words, to prevent storage of a generator that re-generates anomalous data that can already be generated by the stored generator, the stored generator is used to train the discriminator even during the process of training. With this configuration, it is possible to reduce a training time and perform training while correcting training of the discriminator, so that it is possible to improve the discrimination performance of the discriminator.

System

The processing procedures, control procedures, specific names, and information including various kinds of data and parameters illustrated in the above-described document and drawings may be arbitrarily changed unless otherwise specified.

Further, the components of the apparatuses illustrated in the drawings are functionally conceptual and need not necessarily be physically configured in the manner illustrated in the drawings. In other words, specific forms of distribution and integration of the apparatuses are not limited to those illustrated in the drawings. Namely, all or part of the apparatuses may be functionally or physically distributed or integrated in arbitrary units depending on various loads or use conditions. For example, the training processing unit 30, the retraining unit 40, and the detecting unit 50 may be implemented by different apparatuses.

Furthermore, for each processing function performed by each apparatus, all or any part of the processing function may be implemented by a CPU and a program analyzed and executed by the CPU or may be implemented as hardware by wired logic.

Hardware

Figure 16:
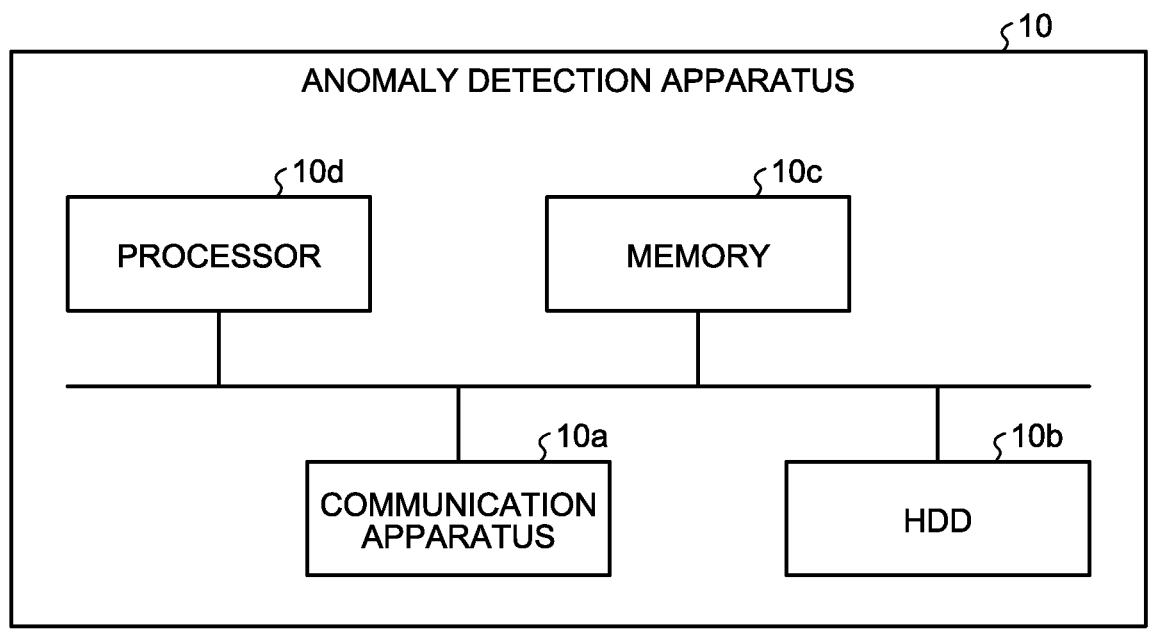
FIG. 16 is a diagram for explaining a hardware configuration example.
Figure 17:
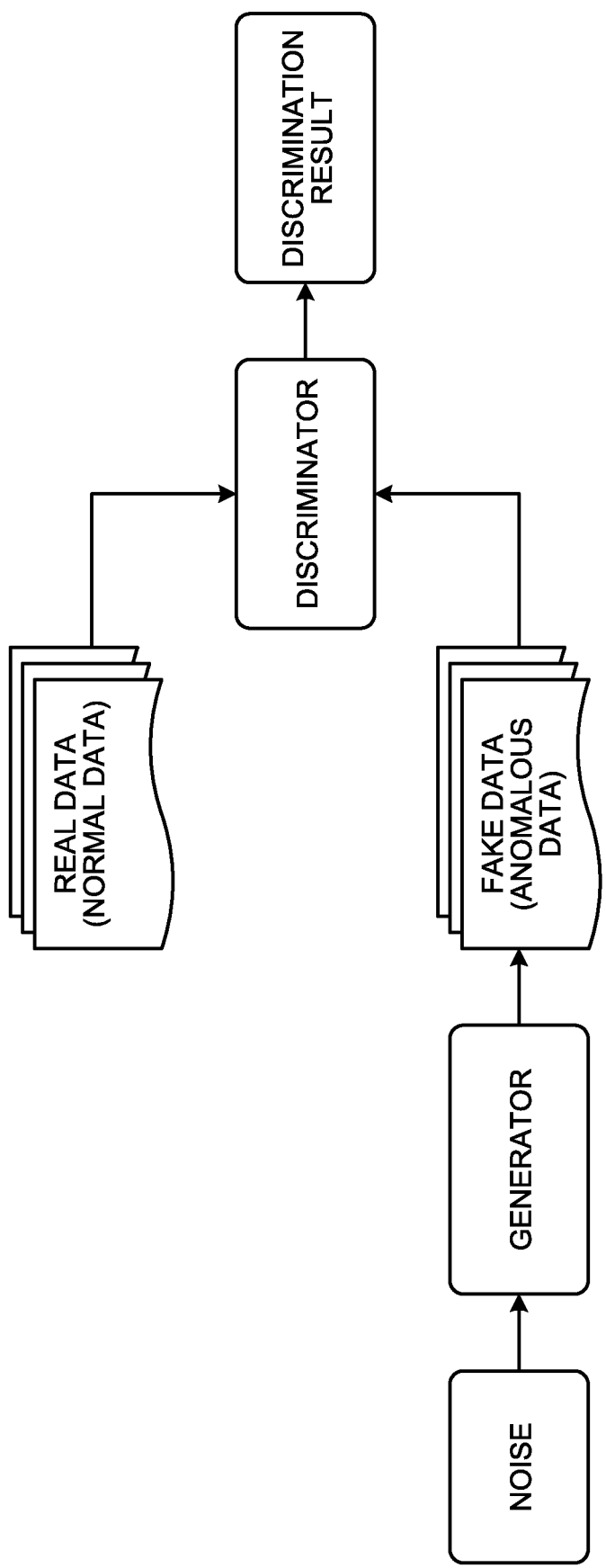
FIG. 17 is a diagram for explaining a GAN.

FIG. 16 is a diagram for explaining a hardware configuration example. As illustrated in FIG. 16, the anomaly detection apparatus 10 includes a communication apparatus 10a, a hard disk drive (HDD) 10b, a memory 10c, and a processor 10d. All of the units illustrated in FIG. 16 are connected to one another via a bus or the like.

The communication apparatus 10a is a network interface card or the like, and performs communication with other servers. The HDD 10b stores therein a program for operating the functions as illustrated in FIG. 6 and DBs.

The processor 10d reads a program for executing the same process as that of each of the processing units illustrated in FIG. 6 from the HDD 10b or the like, and loads the program on the memory 10c, so that the process for implementing each of the functions described with reference to FIG. 6 etc. are operated. In other words, the process implements the same functions as those of all of the processing units included in the anomaly detection apparatus 10. Specifically, the processor 10d reads, from the HDD 10b or the like, a program that has the same functions as those of the training processing unit 30, the retraining unit 40, the detecting unit 50, and the like. Then, the processor 10d performs the process for implementing the same processes as those of the training processing unit 30, the retraining unit 40, the detecting unit 50, find the like.

In this manner, the anomaly detection apparatus 10, by reading and executing the program, functions as the information processing apparatus that performs an anomalous detection method. Furthermore, the anomaly detection apparatus 10 may be able to cause a medium reading device to read the above-described program from a recording medium and execute the read program, to thereby implement the same functions as those of the embodiments as described above. Meanwhile, the program described in the other embodiments need not always be executed by the anomaly detection apparatus 10. For example, the present invention can be applied in the same manner when a different computer or a different server executes the program or the different computer and the different server execute the program in a cooperative manner.

According to the embodiments, it is possible to prevent reduction of the capability of a discriminator to detect anomalies.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A training apparatus comprising:
a memory; and
a processor coupled to the memory, wherein
the processor is configured to:
generate image data using a generator;
discriminate, by a discriminator, whether image data inputted thereto is real or fake, wherein as the discriminator a first discriminator and a second discriminator are provided, for the second discriminator a faster training speed than a training speed of the first discriminator being set;
train the generator so as to maximize a discrimination error of the first discriminator, train the first discriminator so as to minimize the discrimination error of the first discriminator, and train the second discriminator so as to minimize a discrimination error of the second discriminator;
store in the memory a state of the generator when a loss of the second discriminator increases and thereafter starts to decrease and when a loss of the first discriminator is equal to or larger than a threshold, wherein when the stored state is later used for the generator, the generator when the state is stored is reproduced; and
retrain the second discriminator, after the second discriminator is trained to be able to discriminate whether image data inputted thereto is real or fake, by using image data generated by the generator reproduced by the stored state.

2. The training apparatus according to claim 1, the processor is further configured to, when discrimination target image data is divided into a plurality of regions and input to the second discriminator for which the retraining is performed, and when the second discriminator detects an anomaly in a region, present the region to a user.

3. A training method comprising:
generating image data using a generator and discriminating, by a discriminator, whether image data inputted thereto is real or fake, wherein as the discriminator a first discriminator and a second discriminator are provided, for the second discriminator a faster training speed than a training speed of the first discriminator being set, using a processor;
training the generator so as to maximize a discrimination error of the first discriminator, using the processor;
training the first discriminator so as to minimize the discrimination error of the first discriminator, and training the second discriminator so as to minimize a discrimination error of the second discriminator, using the processor;
storing a state of the generator when a loss of the second discriminator increases and thereafter starts to decrease and when a loss of the first discriminator is equal to or larger than a threshold, wherein when the stored state is later used for the generator, the generator when the state is stored is reproduced, using the processor; and
retraining the second discriminator, after the second discriminator is trained to be able to discriminate whether image data inputted thereto is real or fake, by using image data generated by the generator reproduced by the stored state, using the processor.

4. A non-transitory computer-readable recording medium having stored therein a training program that causes a computer to execute:
generating image data using a generator and discriminating, by a discriminator, whether image data inputted thereto is real or fake, wherein as the discriminator a first discriminator and a second discriminator are provided, for the second discriminator a faster training speed than a training speed of the first discriminator being set;
training the generator so as to maximize a discrimination error of the first discriminator;
training the first discriminator so as to minimize the discrimination error of the first discriminator, and training the second discriminator so as to minimize a discrimination error of the second discriminator;
storing a state of the generator when a loss of the second discriminator increases and thereafter starts to decrease and when a loss of the first discriminator is equal to or larger than a threshold, wherein when the stored state is later used for the generator, the generator when the state is stored is reproduced; and
retraining the second discriminator, after the second discriminator is trained to be able to discriminate whether image data inputted thereto is real or fake, by using image data generated by the generator reproduced by the stored state.

* * * * *